United States Patent
Van den Heuvel et al.

(10) Patent No.: US 11,252,520 B2
(45) Date of Patent: Feb. 15, 2022

(54) SUBCUTANEOUS MICROPHONE HAVING A CENTRAL PILLAR

(71) Applicant: Cochlear Limited, Macquarie University (AU)

(72) Inventors: Koen Erik Van den Heuvel, Hove (BE); Patrik Kennes, Herent (BE)

(73) Assignee: Cochlear Limited, Macquire University (AU)

(*) Notice: Subject to any disclaimer, the term of this patent is extended or adjusted under 35 U.S.C. 154(b) by 0 days.

(21) Appl. No.: 16/757,458

(22) PCT Filed: Oct. 16, 2018

(86) PCT No.: PCT/IB2018/058017
§ 371 (c)(1),
(2) Date: Apr. 20, 2020

(87) PCT Pub. No.: WO2019/082021
PCT Pub. Date: May 2, 2019

(65) Prior Publication Data
US 2021/0195350 A1    Jun. 24, 2021

Related U.S. Application Data

(60) Provisional application No. 62/576,021, filed on Oct. 23, 2017.

(51) Int. Cl.
*H04R 7/26* (2006.01)
*H04R 25/00* (2006.01)
*H04R 7/24* (2006.01)

(52) U.S. Cl.
CPC .......... *H04R 25/606* (2013.01); *H04R 7/24* (2013.01); *H04R 25/554* (2013.01); *H04R 2225/67* (2013.01); *H04R 2410/00* (2013.01)

(58) Field of Classification Search
CPC . H04R 1/222; H04R 1/44; H04R 7/24; H04R 2225/67
See application file for complete search history.

(56) References Cited

U.S. PATENT DOCUMENTS 5,859,916 A * 1/1999 Ball .................. H04R 25/606
                                                381/326
6,736,771 B2   5/2004 Sokolich
(Continued)

FOREIGN PATENT DOCUMENTS

KR   100896448 B1   5/2009

OTHER PUBLICATIONS

International Search Report received in related application PCT/IB2018/058017, dated Feb. 28, 2019, (14 pages).

*Primary Examiner* — Ryan Robinson
(74) *Attorney, Agent, or Firm* — Edell, Shapiro & Finnan, LLC

(57) ABSTRACT

In a subcutaneous microphone used in medical devices, a structure is introduced that constrains the motion of the diaphragm during normal operation of the microphone. In one embodiment, a raised portion, such as a pole or pillar is placed in the chamber at the middle of the diaphragm. The raised portion may contact one or both of the bottom surface of the chamber and the underside of the membrane, and generally acts to reduce the amount of deflection experienced by the membrane.

27 Claims, 8 Drawing Sheets

(56) References Cited

U.S. PATENT DOCUMENTS

| | | | |
|---|---|---|---|
| 7,204,799 B2* | 4/2007 | Miller, III | A61N 1/36038 |
| | | | 600/25 |
| 7,241,258 B2* | 7/2007 | Miller, III | H04R 25/604 |
| | | | 181/175 |
| 7,903,836 B2 | 3/2011 | Miller, III | |
| 8,200,339 B2* | 6/2012 | Wiskerke | H04R 1/08 |
| | | | 607/57 |
| 8,509,469 B2* | 8/2013 | Miller, III | H04R 25/606 |
| | | | 381/361 |
| 8,721,518 B2* | 5/2014 | Hellmuth | H04R 25/606 |
| | | | 600/25 |
| 8,894,562 B2* | 11/2014 | Zahnert | H04R 25/606 |
| | | | 600/25 |
| 8,929,584 B2* | 1/2015 | Zoellin | H04R 7/24 |
| | | | 381/429 |
| 9,066,185 B2* | 6/2015 | Koskowich | H04R 25/606 |
| 9,066,187 B2* | 6/2015 | van Halteren | H04R 1/326 |
| 9,462,389 B2* | 10/2016 | Wang | H04R 7/16 |
| 2007/0009132 A1 | 1/2007 | Miller | |
| 2008/0167516 A1 | 7/2008 | Jaeger | |
| 2011/0144415 A1 | 6/2011 | Hellmuth | |
| 2015/0110302 A1* | 4/2015 | Chen | B81C 1/00182 |
| | | | 381/162 |
| 2017/0208390 A1 | 7/2017 | Larsen et al. | |

* cited by examiner

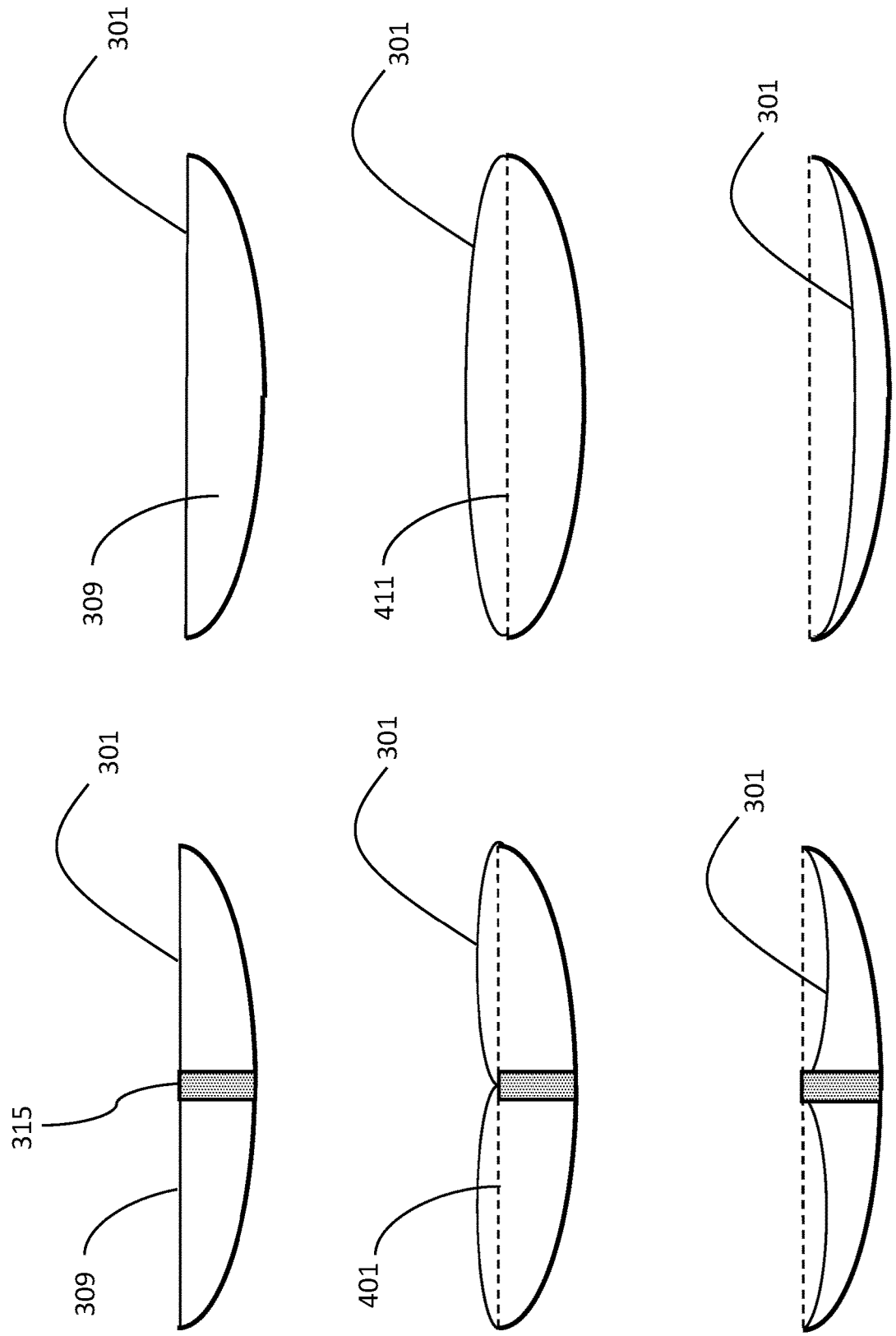

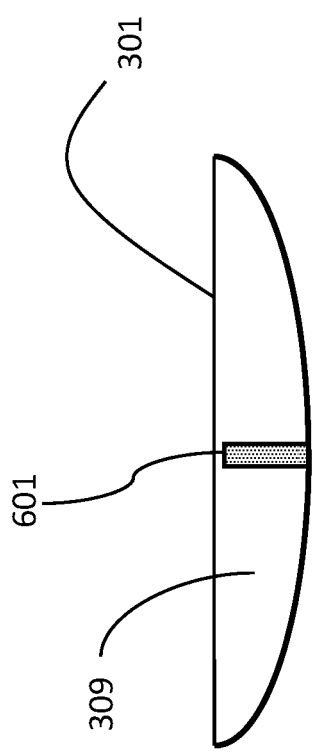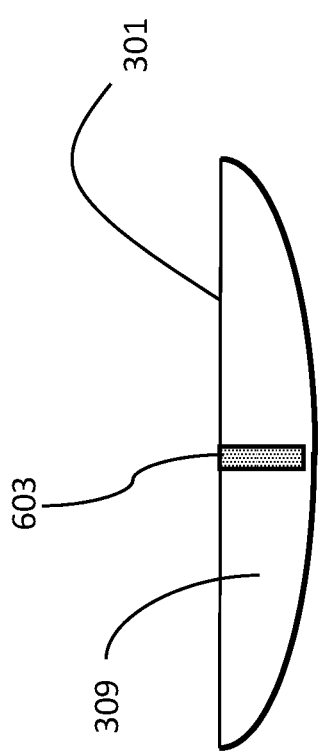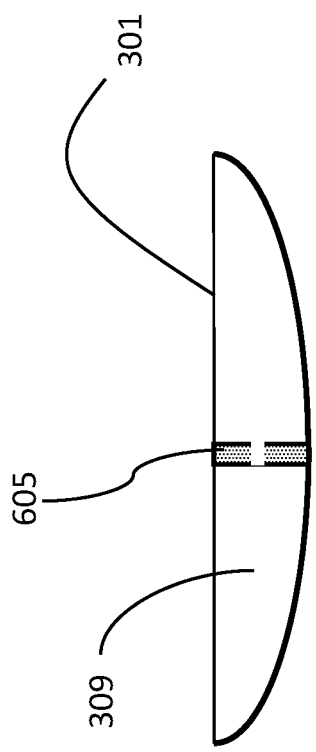

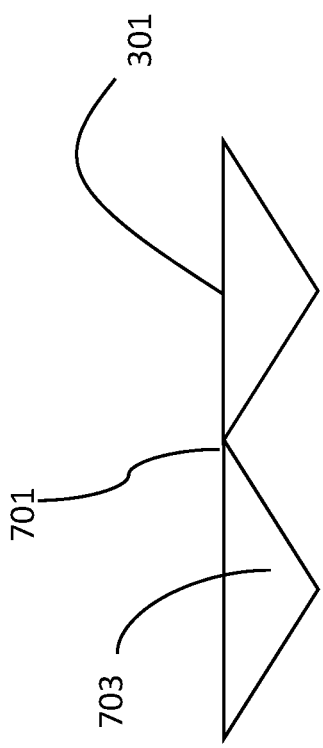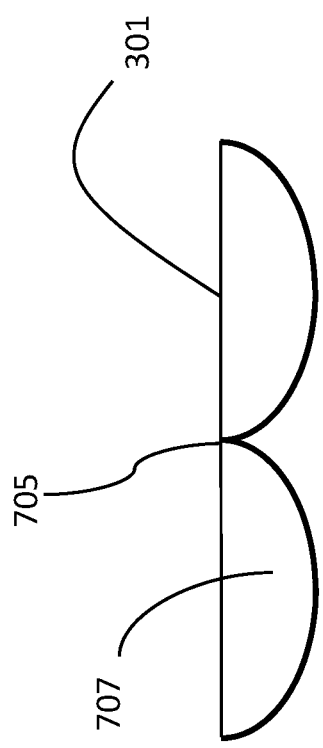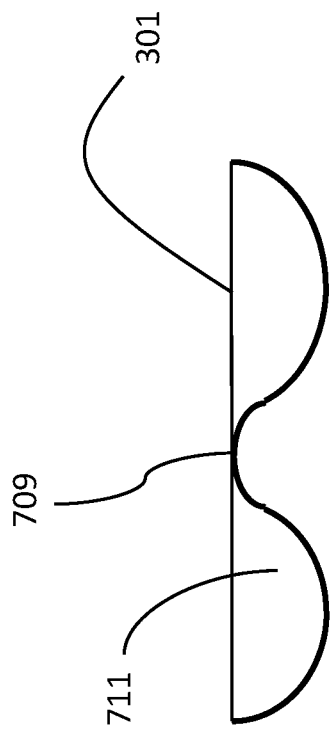

SUBCUTANEOUS MICROPHONE HAVING A CENTRAL PILLAR

TECHNICAL FIELD

The technology described herein generally relates to subcutaneous microphones used in medical devices.

BACKGROUND

Hearing loss, which can have many different causes, is generally of two types: sensorineural and conductive. Sensorineural hearing loss is due to the absence or destruction of the hair cells in the cochlea which transduce sound signals into nerve impulses. Various commercially available hearing prostheses can provide individuals suffering from sensorineural hearing loss with the ability to perceive sound. For example, cochlear implants use an electrode array implanted in a recipient's cochlea to bypass the ear's normal mechanism. In a cochlear implant, the electrode array delivers an electrical stimulus to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing if the hair cells in the cochlea are undamaged.

Sufferers of conductive hearing loss are typically treated by providing them with an acoustic hearing aid. This type of hearing aid relies on principles of air conduction to transmit acoustic signals to the cochlea. In particular, an acoustic hearing aid typically uses an arrangement positioned in the recipient's ear canal or on the outer ear to amplify a sound received at the outer ear of the recipient. This amplified sound is transmitted to the cochlea where it causes the normal motion of the perilymph and stimulation of the auditory nerve.

In contrast to acoustic hearing aids, which rely primarily on air conduction, certain types of hearing prostheses, commonly referred to as bone conduction devices, convert a received sound into vibrations. The vibrations are transferred through the skull to the cochlea causing generation of nerve impulses, which result in the recipient's perception of the received sound. Bone conduction devices are suitable to treat a variety of types of hearing loss and may be suitable for individuals who cannot derive sufficient benefit from acoustic hearing aids or cochlear implants, or for individuals who suffer from stuttering problems.

The current trend in hearing aid technology is towards partially, or fully implanted devices that thereby free the recipient from the inconvenience and unsightliness of wearing a visible and often conspicuous device. When fitted with an implantable auditory prosthesis, people look completely normal; their appearance does not betray a hearing impediment.

Throughout the description and claims of the application the word "comprise" and variations thereof, such as "comprising" and "comprises", is not intended to exclude other additives, components, integers or steps.

SUMMARY

The instant disclosure addresses an implantable microphone comprising a diaphragm, and a housing having a rim and a recessed interior, such that the diaphragm is supported by the rim of the housing. In some embodiments, a central raised portion of the recessed interior also supports the diaphragm; in other embodiments, a central pillar extends from the underside of the diaphragm and contacts the surface of the recessed interior during normal operation; in yet other embodiments, a supportive central structure is included within the housing to constrain the motion of the diaphragm during normal operation of the microphone. The central raised portion can take a number of forms, including a pillar or a conical structure extending from the bottom of the recessed interior to the underside of the diaphragm. The implantable microphone having such a central raised portion can have a resonance frequency that is shifted to a higher frequency relative to an implantable microphone having a housing without a central raised portion.

The housing can have a cross section—as measured for example in a plane along a diameter and perpendicular to the diaphragm—selected from: rectangle, triangle, parabola, portion bounded by an arc of a circle or ellipse.

The implantable microphone can find itself as part of a fully implantable acoustic device as well as a totally implantable cochlear implant. As such the implantable microphone can be configured to facilitate mitigating hearing loss for the hearing impaired.

BRIEF DESCRIPTION OF THE DRAWINGS

FIGS. 4A and 4B show variations of diaphragm position in two subcutaneous microphones, and conveys how a subcutaneous microphone in accordance with certain embodiments of the invention can perform relative to a conventional subcutaneous microphone.

FIGS. 6A-6C show embodiments of a subcutaneous microphone having a central pillar.

FIGS. 7A-7C show embodiments of a subcutaneous microphone having various forms of raised central portion.

Like reference symbols in the various drawings indicate like elements.

DETAILED DESCRIPTION

Figure 1:
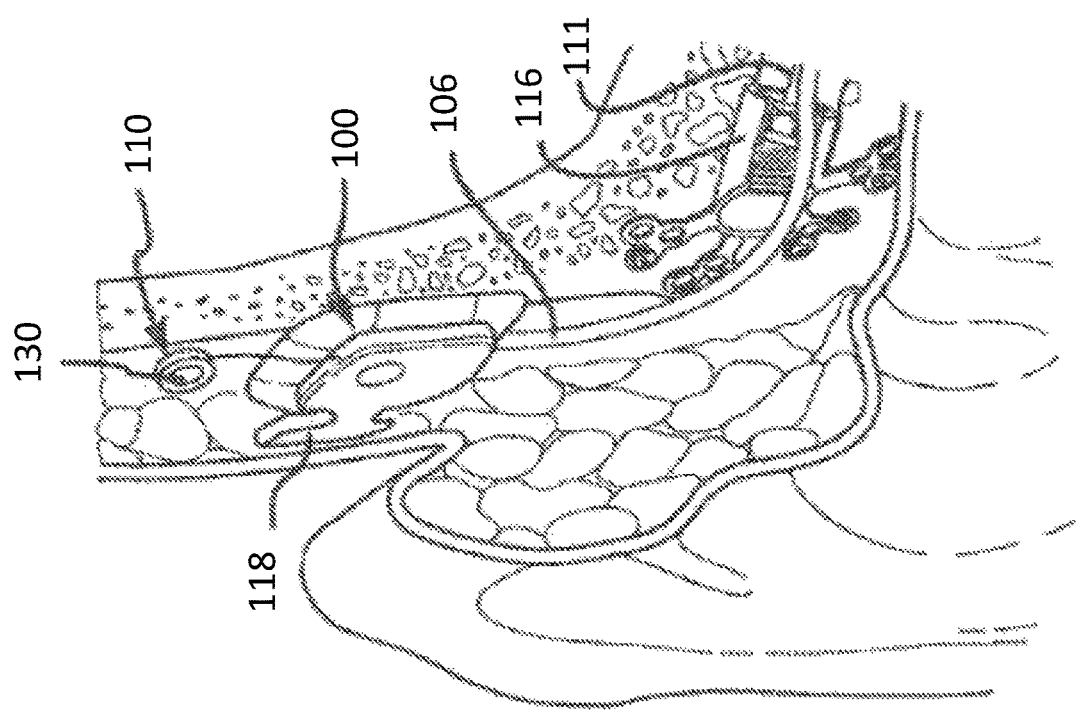
FIG. 1 shows an environment for an implantable auditory prosthesis that provides mechanical stimulation to a recipient's middle ear, and is suitable for use with the instant technology.

Many implantable auditory prostheses contain a subcutaneous microphone, implanted close to the recipient's skull and typically above and behind the ear. Such a microphone, which is just one component of many implanted pieces of the auditory prosthesis, must pick up sounds that are attenuated by passage through the recipient's skin tissue in order to transmit sounds to the recipient's inner ear. Consequently, microphones of implanted hearing aids are larger than those of external hearing aids.

In order to maximize the amount of ambient sound that is detected by implanted microphones, their positioning, size, and shape can be optimized.

Many microphone designs use a diaphragm positioned over a circular chamber. Sounds in the vicinity of the recipient create vibrations of the skin tissue that is in contact with the diaphragm, which in turn vibrates and creates pressure variations within the chamber. The pressure variations can be transmitted via other components of the auditory prosthesis to the recipient's inner ear. The diaphragm is only supported around the outside rim of the chamber, and the interior of the chamber comprises a cavity that has certain properties such as a resonant frequency.

The trade-off that has been present in the devices in the art is between sensitivity and resonant frequency: the larger the diaphragm the greater the microphone's sensitivity. Thus, whereas external microphones may have diaphragms as small as 1-2 mm in diameter, implanted microphones are considerably larger because they must detect sound that has been modulated by a thickness of the recipient's skin. Conversely, as the cavity size increases, the resonant frequency decreases (there being an inverse proportionality between the two) and the microphone becomes better tuned for low frequency sounds (sometimes as low as 2-3 Khz). But sounds in the lower range of the frequency spectrum—which may include sub-audible sounds—are typically not the sounds that a recipient wants to hear clearly, and normal everyday sounds such as speech become poorly transmitted by the microphone or contain a lot of noise and are therefore poorly comprehended by the recipient.

Furthermore, as the diaphragm increases in size, it can be hard to manufacture to an even thickness, and may be susceptible to pressure variations across its area, meaning that it can distort a sound that it receives.

Current microphones are also susceptible to a different problem: their behavior as a result of significant changes in ambient pressure, such as when the recipient goes up a mountain or flies in a plane, or dives in a pool. In normal microphones, such as those not implanted in a recipient, there is the same air pressure on both sides of the membrane. By contrast, the diaphragm of an implanted microphone is attached on one side to a completely closed cavity. For example, the remainder of the microphone may be contained within a hermetically sealed titanium housing so that body fluids do not seep into the microphone. But the diaphragm is also in contact with the recipient's flesh on its other side. Therefore, the membrane moves as a result of external pressure changes. If the changes are great enough to fully depress the membrane, it may contact the other side of chamber, which is undesirable.

The disclosure includes a subcutaneously implanted microphone that has a compact diaphragm coupled with a chamber that has been modified to improve the microphone's performance when facing pressure variation.

In many embodiments, a subcutaneous microphone includes a centralized structure configured to constrain the motion of the diaphragm during normal operation. In a number of embodiments, the centralized structure takes the form of a raised portion situated in the center of the chamber and extending from the bottom of the cavity to the underside of the diaphragm. This raised portion can increase the resonance frequency of the microphone relative to a microphone having a cavity of the same size and shape, and therefore can permit a smaller microphone cavity to be deployed. The raised portion can further provide support for the diaphragm, thereby removing the possibility that the diaphragm could itself make contact with the bottom of the cavity at the greatest extent of its vibrational motion.

Figure 2:
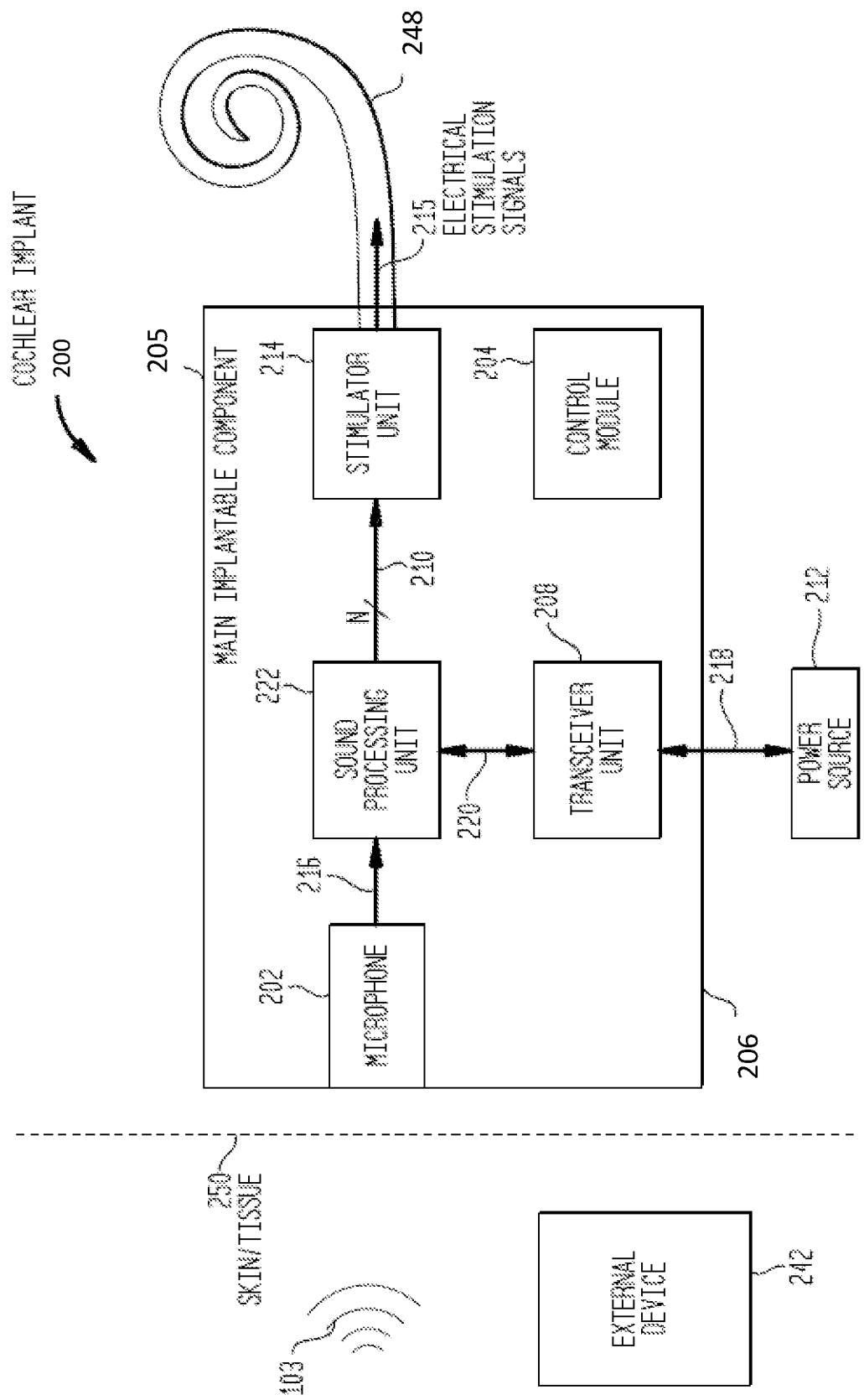
FIG. 2 shows schematically a totally implantable cochlear implant suitable for use with the instant technology.

FIGS. 1 and 2 show examples of two different types of device that can benefit from the technology herein. FIG. 1 shows an acoustic device that provides relief from conductive hearing loss, and FIG. 2 shows a cochlear implant that addresses sensorineural hearing loss. Both types of system are examples of auditory prostheses that can be improved by any of the various subcutaneous microphones disclosed herein.

In FIG. 1, a biocompatible implant housing 100 of a middle ear implant is located subcutaneously on a patient's skull. An example of such an implant is the Carina™ device, available from Cochlear Limited, Sydney, Australia. The implant housing 100 includes a signal receiver 118 (e.g., comprising a coil element) and may include an integrated microphone or a separate implantable microphone 110 that is interconnected to the housing 100 via an electrical connector. In either case, microphone 110 will include a diaphragm 130 that is positioned to receive acoustic signals through overlying tissue. Typically the thickness of the skin tissue on top of the microphone is 6 mm, though the range of thickness can be from 2-10 mm. The diaphragm 130 is typically made of a strong metal that is resistant to corrosion, such as titanium.

Typically, the signal processor within the implant housing 100 is electrically interconnected via wire 106 to a transducer (not shown). A positioning system 116 is connected to a bone anchor mounted within the patient's mastoid process (e.g., via a hole drilled through the skull). During normal operation, acoustic signals are received subcutaneously at the microphone 110, which generates signals for receipt by the housing 100. Upon receipt of the signals, a signal processor within the implant housing 100 processes the signals to provide a processed audio drive signal via wire 106 to the transducer 111. Positioning of the microphone, in a bone recess, can be accomplished by a routine surgical procedure.

FIG. 2 shows schematically a block diagram of a totally implantable cochlear implant system 200. Totally implanted devices can have a coil/magnet configuration to facilitate coupling with an external component or device 242 such as a charger, or an external sound processor for use in difficult hearing environments.

In system 200, all components are configured to be implanted under one or more layers of skin tissue 250 of a recipient. Therefore, system 200 operates, for at least some of the time, without the need of an external device. An external device 242 can be used to charge an internal battery 212, to supplement the performance of the implanted microphone 202, or when the internal battery no longer functions. External device 242 can be secured in place via a magnetic coupling with a magnet in the implanted portion.

System 200 includes a main implantable component 205 having a hermetically sealed, biocompatible housing 206. Disposed in main implantable component 205 is a microphone 202 configured to sense a sound signal 103. Microphone 202 may include one or more components to pre-process the microphone output.

An electrical signal 216 representing sound signal 103 detected by microphone 202 is provided from the microphone to sound processing unit 222. Sound processing unit 222 implements one or more speech processing and/or coding strategies to convert the pre-processed microphone output into data signals 210 for use by stimulator unit 214. Stimulator unit 214 utilizes data signals 210 to generate electrical stimulation signals 215 for delivery to the cochlea of the recipient (not shown). In the example of FIG. 2, a stimulating electrode assembly 248 delivers signal 215 to the cochlea.

Cochlear implant system 200 also includes a power source 212. Power source 212 may comprise, for example, one or more rechargeable batteries. Power can be received from a suitably positioned external device 242 and stored in power source 212. The power may then be distributed 218 to the other components of system 200 as needed for operation. For ease of illustration, main implantable component 205 and power source 212 are shown separate from one another. However, power source 212 can alternatively be integrated into the hermetically sealed housing 206, or can be part of a separate module coupled to component 205.

Main implantable component 205 further comprises a control module 204, which can include various components for controlling the operation of implant 200, or specific components of it. For example, controller 204 may control the delivery of power from power source 212 to other components of cochlear implant system 200.

Cochlear implant system 200 further comprises a receiver or transceiver unit 208 that permits the system to transcutaneously receive and/or transmit signals 226 such as power and/or data to/from an external device 242. For example, signals representative of sound detected by an external microphone (not shown) can be transmitted from external device 242 to receiver or transceiver unit 208, and subsequently conveyed to sound processing unit 222 as demodulated or decoded signal 220.

As used herein, transceiver unit 208 refers to any collection of one or more implanted components which form part of a transcutaneous energy transfer system. Further, transceiver unit 208 includes any number of component(s) which receive and/or transmit data or power, such as, for example, a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data 226 from external device 242 to implantable component 205. To optimize such transfer, external device 242 is typically magnetically aligned with implantable component 205.

For ease of illustration, cochlear implant system 200 is shown having a transceiver unit 208 in main implantable component 205. In alternative arrangements (not shown), cochlear implant system 200 includes a receiver or transceiver unit which is implanted elsewhere in the recipient outside of main implantable component 205.

Exemplary Embodiments

Figure 3A:
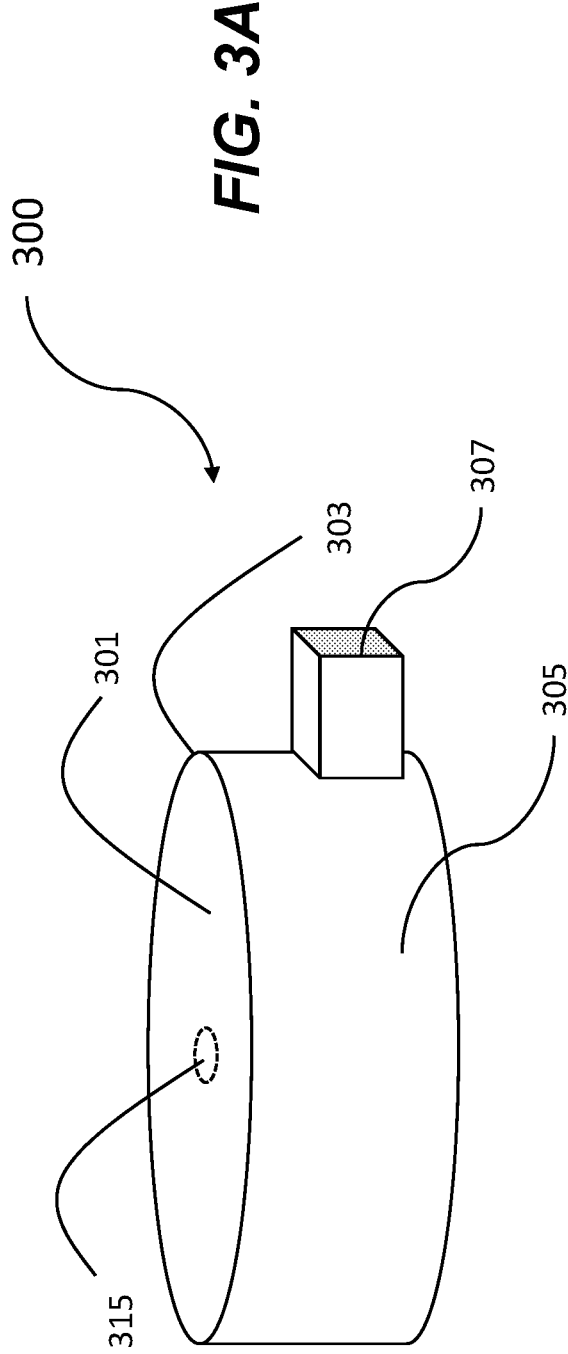
FIGS. 3A and 3B show views of a subcutaneous microphone in accordance with certain embodiments of the invention.
Figure 3B:
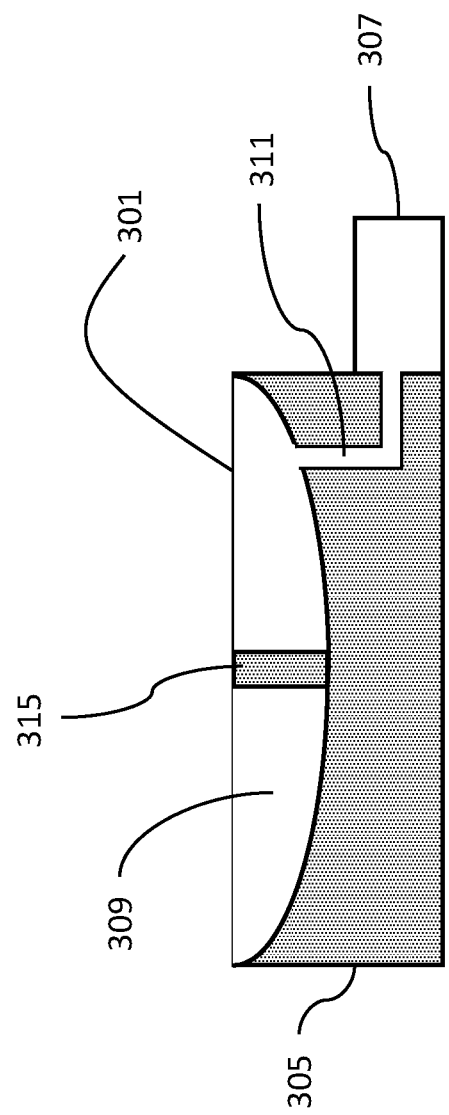

FIGS. 3A and 3B show a first embodiment of a subcutaneous microphone 300 having the improvements described herein. FIG. 3A shows the microphone in perspective view, and FIG. 3B shows a cross-sectional view of the microphone taken from a plane that bisects the midpoint of the diaphragm.

Microphone 300 has a diaphragm 301 which is typically circular and is attached at its circumference 303 to the upper rim of a chamber 309 contained within housing 305. The interior of chamber 309 and the diaphragm 301 form a cavity, which is typically radially symmetric. The cavity formed by the diaphragm and the housing together typically has a volume in the range 0.01 to 10 mm$^3$, although, of course, a cavity of any suitable volume can be implemented in accordance with embodiments of the invention.

Electronic components 307 receive a sound as a change in air pressure in the chamber, and process it, such as amplify it, so that it can be directed to the recipient's auditory system. The components 307 are shown mounted to the outside of housing 305 but in other embodiments they may be positioned within the housing 305. Components 307 typically include an electric diaphragm that acts as a pressure sensor. Sound from the recipient's skin is transmitted via diaphragm 301 and can be amplified by the small diaphragm of the pressure sensor by as much as 20 dB.

In FIGS. 3A and 3B, and subsequent figures, the depth of the cavity is exaggerated relative to the other dimensions in the figures: the cavity can be only a few 10's of microns in thickness, for example, 75 microns, which is comparable to the diaphragm thickness. Correspondingly, the diaphragm diameter can typically be from 4-16 mm and more typically 8-12 mm, though ideally may be as small as 4 mm. Typical diaphragm thicknesses can be in the range 0.01 mm to 0.15 mm.

The separation between the diaphragm and the bottom of the recessed cavity can typically be from 0.002 to 0.1 cm. Of course, it should be appreciated that while certain dimensions have been referenced, subcutaneous microphones having any suitable dimensions can be implemented in accordance with embodiments of the invention.

As shown in the cross-sectional view of FIG. 3B, the chamber 309 has a concave interior that has a small lumen 311 connecting it to the sensor within the electronics 307. Lumen 311 is shown as having a right-angled shape but it can take other geometries (not shown), such as curved or straight, or with more than one corner in accordance with many embodiments of the invention.

Chamber 309 further has a central pillar 315 disposed between the bottom of the interior of the chamber and touching the underside of the diaphragm. Pillar 315 may be welded or glued to the underside of the membrane and to the bottom of the cavity. Any suitable technique for affixing pillar 315 to the membrane and bottom of the cavity may be implemented. Pillar 315 is typically as tall as the thickness of the cavity, e.g., is only a few 10's of microns tall.

Pillar 315 is shown as having a circular cross-section (i.e., is a right cylinder) in the embodiment of FIGS. 3A and 3B, but other shapes of pillar 315 are within the scope of the instant disclosure and are illustrated and described with respect to embodiments discussed elsewhere herein.

FIGS. 4A and 4B show variations of the position of the diaphragm according to variations in ambient pressure, in respectively a microphone having a central pillar in accordance with certain embodiments of the invention and one without. In FIGS. 4A and 4B, there are three views corresponding to pressures at sea level (top), high altitude or low pressure (middle), and under water or high pressure (bottom). In the middle and bottom views a dashed line 401 represents the position of the undisturbed diaphragm. In each case it can be seen that the central pillar prevents the diaphragm from potentially contacting the bottom interior surface of the chamber. The fact that a smaller area of diaphragm, overall, is subject to deflection in FIG. 4A means that the resonance frequency of the cavity is increased relative to that of FIG. 4B.

It can be seen that the diaphragm of the embodiment having a central pillar is constrained by the central pillar and does not deflect from its resting position at that point of contact. It can also be seen (though the panels of FIGS. 4A and 4B are not drawn to scale) that the amount of vertical deflection of the diaphragm in FIG. 4A is less than that of the unconstrained diaphragm in FIG. 4B.

Figure 5B:
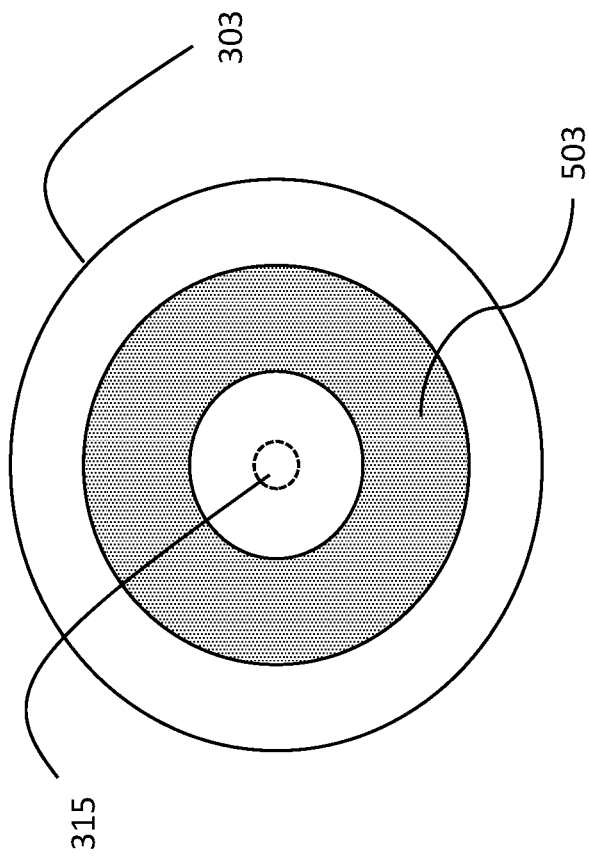
FIGS. 5A and 5B show views of active areas of a diaphragm of two subcutaneous microphones, and conveys how a subcutaneous microphone in accordance with certain embodiments of the invention can perform relative to a conventional subcutaneous microphone.
Figure 5A:
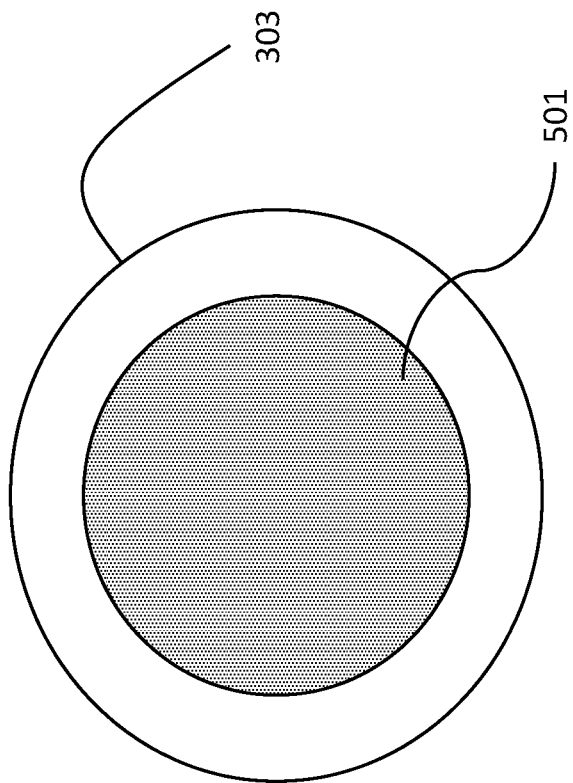

FIGS. 5A and 5B show elevated views of a diaphragm of a subcutaneous microphone, respectively, with and without a central pillar. The outer edge of the membrane 303 is shown in each case. The top of the central pillar 315 is shown in the microphone of FIG. 5B. The shaded regions of the two diaphragms, 501 and 503 respectively, correspond to the regions that actively respond to sounds. The fact that the diaphragm in the embodiment with the central pillar does not have as large an active area (i.e., does not move as much overall relative to a microphone having a diaphragm of the same size but without a central pillar) can lead to reduced sensitivity at some frequencies, even though the overall bandwidth can be increased. Typically, sensitivity is improved at the higher frequencies detected by the human ear, even though sensitivity at the lower frequencies can be decreased. A thinner membrane can be implemented to counteract any reduction in sensitivity caused by the introduction of a central constraining structure in accordance with many embodiments of the invention. For example, in many embodiments, a diaphragm having a thickness that is between approximately 50% and approximately 75% relative to that of a conventional membrane may be implemented to improve sensitivity (e.g., if typical diaphragm thicknesses range from 0.01 mm to 0.15 mm, then diaphragms having thicknesses of between approximately 50% and 75% of those values can be implemented). Of course, a membrane of any appropriate thickness that can mitigate any sensitivity reduction caused by the included centralized structure can be implemented in accordance with embodiments of the invention. Alternatively, the diameter of the membrane relative to that of a microphone without a central pillar can be increased.

Although specific shapes and dimensions have been referred to with respect to FIGS. 3A, 3B, 4A, 4B, 5A, and 5B, it should be clear that the scope of the invention is not limited to those embodiments explicitly depicted and described. Rather, any of a variety of suitable geometries having suitable dimensions can be used to effectuate the teachings of the instant application.

FIGS. 6A, 6B, and 6C show embodiments of a subcutaneous microphone in which a central pillar contains a break or cut-out so that it does not extend continuously for the entire distance between the bottom of the cavity and the underside of the diaphragm. In such embodiments, the central pillar protects the microphone from a malfunction that would arise if the membrane deflected enough to contact the bottom of the cavity, but limits the range of deflection of the membrane. In the embodiment of FIG. 6B, the central pillar is attached to the underside of the membrane but does not contact the bottom of cavity at normal pressures. In the embodiment of FIG. 6A, the central pillar is mounted on the bottom of cavity but does not contact the underside of the membrane at normal pressures. In FIG. 6C, the central pillar is in two parts, one of which is mounted on the bottom of the cavity, and one of which is disposed on the underside of the membrane. The two parts of the pillar in FIG. 6C do not contact one another at normal pressures, and only do if the diaphragm is sufficiently deflected.

The central pillar can be made from materials such as titanium; a titanium alloy; a glue such as epoxy or UV-cured epoxy; and soft silicone. But of course, the central pillar can be made from any of a variety of suitable materials, not just those explicitly enumerated.

Although a central pillar has been illustrated and described with respect to FIGS. 3A, 3B, 4A, 4B, 5A, 5B, and 6A-6C, any of a variety of geometries can be used to deter unwanted excessive diaphragm fluctuation in accordance with embodiments of the invention. Non-limiting examples of such structures are shown in FIGS. 7A-7C.

FIGS. 7A-7C depict further embodiments in which there is a raised portion in the center of the cavity, rather than a pillar. The raised portion in the embodiments of FIGS. 7A-7C is formed from the interior shape of the cavity, and is a contiguous part of the bottom of the housing. The views in FIGS. 7A-7C are all of cross sections across a diameter of a radially symmetric chamber. Thus, the chamber has a ring structure when viewed from above.

In FIG. 7A, a conical structure rises from the lower surface of the chamber 703. The apex of the cone touches the underside of the diaphragm 301. Consistent with the embodiment of FIG. 6A, it is possible for the cone to protrude to an apex that is positioned just below the diaphragm (not shown).

In FIG. 7B, the bottom of the chamber 707 rises to form a cusp whose point 705 touches the underside of diaphragm 301. Again, the cusp need not actually touch the underside of the diaphragm, as in other embodiments (not shown).

In FIG. 7C, the bottom of the chamber 711 is a mound having a curved top whose highest point 709 touches the underside of the diaphragm 301. In other embodiments not shown, the mound is narrower or broader and at its highest point is just beneath the level of the diaphragm.

Still other embodiments of a microphone having a chamber with a raised central portion can be contemplated and are consistent with the technology described herein. Any of a variety of architectures can be implemented that embody a centralized structure to eliminate excessive diaphragm movement. In a number of embodiments, the centralized structure is offset from the true center of the cavity.

The subcutaneous microphones herein may be manufactured by methods typically deployed to make other microphones in the art.

The technology described herein can be adapted to work with any type of hearing device that is fitted to a recipient and has a subcutaneous microphone. Such devices include auditory prostheses generally, such as acoustic hearing aids and cochlear implants. The devices include those that work in the middle ear, and various combinations of such hearing device types. The technology herein is also compatible with other hearing devices that are worn off the ear.

EXAMPLES

Example 1: Subcutaneous Microphone Having a Central Pillar

Figure 8:
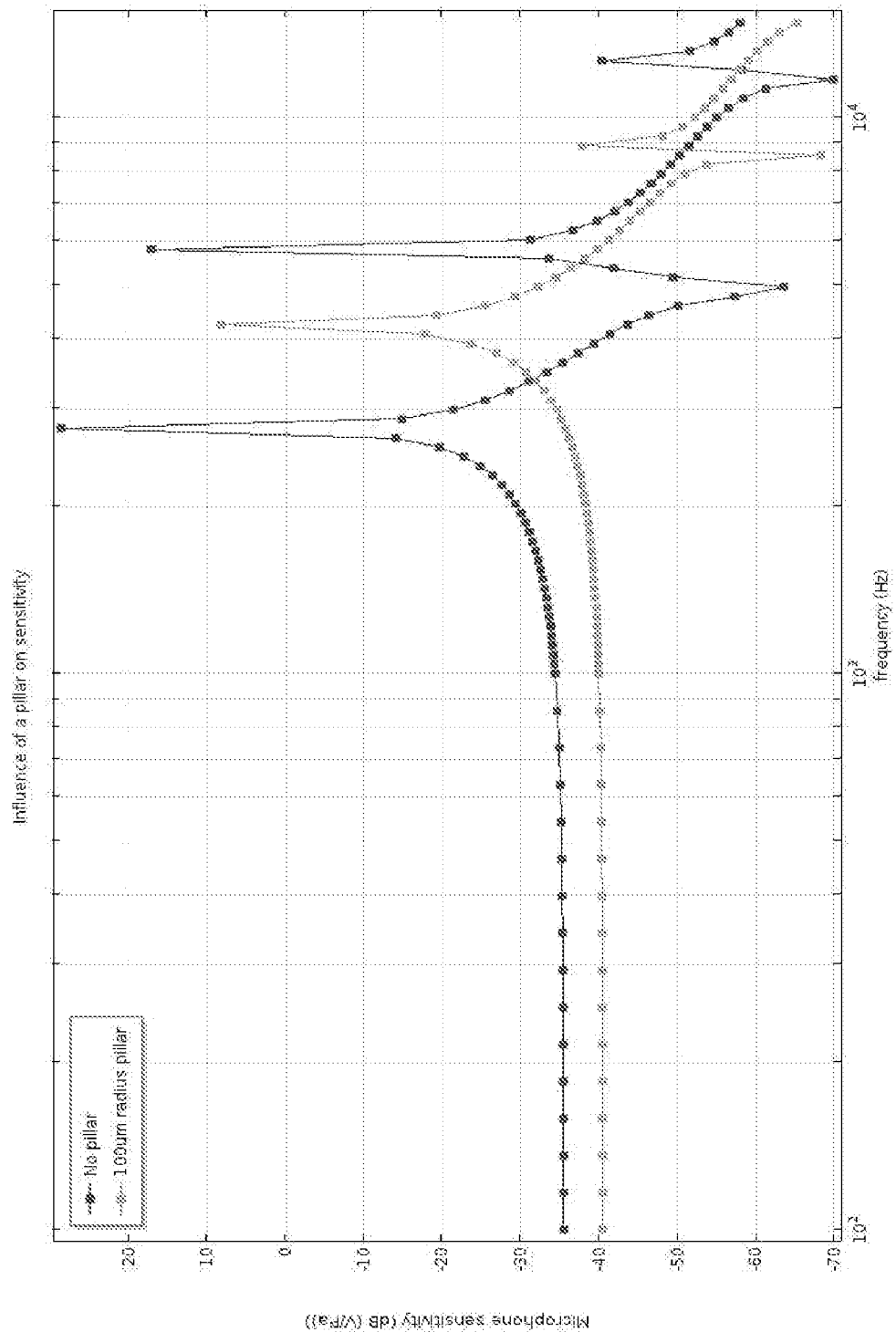
FIG. 8 shows a plot of sensitivity vs. frequency for a subcutaneous microphone having a central pillar in accordance with certain embodiments of the invention relative to that without a central pillar.

Properties of an exemplary subcutaneous microphone having a titanium central pillar of 100 micron radius are shown in FIG. 8. In FIG. 8, a plot of microphone sensitivity against frequency is shown for a subcutaneous microphone having no central pillar, and one having a central pillar made of titanium. The plots are generated computationally and show that the pillar can cause a loss of 5 dB in sensitivity but also shifts the resonance peak frequency by more than 1 kHz. The plots are generated assuming a constant ambient pressure of atmospheric.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the scope of the appended claims.

What is claimed is:

1. An implantable microphone comprising:
a housing comprising a rim and a recessed interior having a central raised portion; and
a diaphragm supported by the rim of the housing and by the central raised portion of the recessed interior, the diaphragm and the housing collectively forming a cavity, and the central raised portion configured to prevent the diaphragm from contacting a bottom of the cavity, and the housing being hermetically sealed for implantation into a recipient.

2. The implantable microphone of claim 1, wherein the central raised portion of the recessed interior is a pillar extending from a bottom of the recessed interior to an underside of the diaphragm.

3. The implantable microphone of claim 1, wherein the central raised portion is made from a material selected from a group comprising: titanium; a titanium alloy; glue; epoxy; and soft silicone.

4. The implantable microphone of claim 1, wherein the central raised portion has a general conical shape with a base disposed on a bottom of the recessed interior and an apex in contact with an underside of the diaphragm.

5. The implantable microphone of claim 1, wherein the recessed interior is radially symmetric and the central raised portion is part of a bottom of the housing.

6. The implantable microphone of claim 1, wherein the diaphragm and the housing together form a cavity having a volume in a range of approximately 0.01 cubic millimeters ($mm^3$) to approximately 10 $mm^3$.

7. The implantable microphone of claim 1, wherein a separation between the diaphragm and a bottom of the cavity is in a range of approximately 0.002 centimeters (cm) to approximately 0.1 cm.

8. The implantable microphone of claim 1, wherein the diaphragm has a general circular shape and has a diameter in a range of approximately 4 millimeters (mm) to approximately 16 mm.

9. The implantable microphone of claim 1, wherein the housing has a cross section shape selected from a group comprising: rectangle, triangle, parabola, portion bounded by an arc of a circle or ellipse.

10. The implantable microphone of claim 1, wherein the implantable microphone has an increased sensitivity relative to an implantable microphone having a housing without a raised portion.

11. A totally implantable cochlear implant comprising the implantable microphone of claim 1.

12. The implantable microphone of claim 1, wherein the central raised portion has a cylindrical shape.

13. The implantable microphone of claim 1, wherein the central raised portion includes at least one cut-out.

14. An implantable microphone, comprising:
a housing having a rim and a central portion; and
a diaphragm supported by the rim and the central portion of the housing, the diaphragm and the housing collectively forming a cavity, and the central portion configured to prevent the diaphragm from contacting a bottom of the cavity, and the housing being hermetically sealed.

15. The implantable microphone of claim 14, wherein the diaphragm has a thickness in a range of approximately 0.01 millimeters (mm) to approximately 0.15 mm.

16. The implantable microphone of claim 14, wherein the central portion is a centrally positioned pillar configured to constrain motion of the diaphragm.

17. The implantable microphone of claim 16, wherein the centrally positioned pillar has a cylindrical shape.

18. The implantable microphone of claim 16, wherein the centrally positioned pillar has a conical shape with an apex in proximate to an underside of the diaphragm.

19. The implantable microphone of claim 16, wherein the centrally positioned pillar has a cut-out.

20. An implantable microphone, comprising:
a housing having a rim and a recessed interior;
a diaphragm attached to the rim of the housing; and
a pillar attached to the diaphragm and configured to constrain motion of the diaphragm in response to sound signals, the diaphragm and the housing collectively forming a cavity, and the pillar configured to prevent the diaphragm from contacting a bottom of the cavity, and the housing being hermetically sealed.

21. The implantable microphone of claim 20, wherein the diaphragm comprises an interior surface and an exterior surface, and wherein the pillar is attached to the interior surface of the diaphragm.

22. The implantable microphone of claim 20, wherein the pillar is a centrally positioned pillar.

23. The implantable microphone of claim 20, wherein the pillar has a cylindrical shape.

24. The implantable microphone of claim 20, wherein the diaphragm has a general circular shape.

25. The implantable microphone of claim 20, wherein the housing is hermetically attached to the diaphragm.

26. A totally implantable cochlear implant comprising the implantable microphone of claim 14.

27. A totally implantable cochlear implant comprising the implantable microphone of claim 20.

* * * * *